US007002688B2

(12) United States Patent
Aravanis et al.

(10) Patent No.: US 7,002,688 B2
(45) Date of Patent: Feb. 21, 2006

(54) MULTILENS OPTICAL ASSEMBLY FOR A DIAGNOSTIC DEVICE

(75) Inventors: Alexander M. Aravanis, Palo Alto, CA (US); Raymond T. Hebert, Los Gatos, CA (US); Bryan E. Loucks, Los Altos Hills, CA (US); John D. Lytle, Santa Cruz, CA (US); Jason L. Pyle, Palo Alto, CA (US)

(73) Assignee: Pria Diagnostics, Inc., Menlo Park, CA (US)

( * ) Notice: Subject to any disclaimer, the term of this patent is extended or adjusted under 35 U.S.C. 154(b) by 0 days.

(21) Appl. No.: 10/865,100

(22) Filed: Jun. 9, 2004

(65) Prior Publication Data

US 2005/0083522 A1    Apr. 21, 2005

Related U.S. Application Data

(63) Continuation-in-part of application No. 10/705,162, filed on Nov. 6, 2003, now Pat. No. 6,929,945.

(60) Provisional application No. 60/511,798, filed on Oct. 16, 2003.

(51) Int. Cl.
*G01N 21/64* (2006.01)
(52) U.S. Cl. .................... 356/417; 250/458.1
(58) Field of Classification Search ............... 356/317, 356/318, 417; 250/458.1, 459.1, 461.1, 461.2
See application file for complete search history.

(56) References Cited

U.S. PATENT DOCUMENTS

| | | | |
|---|---|---|---|
| 4,678,311 A | 7/1987 | Loce et al. | |
| 4,692,015 A | 9/1987 | Loce et al. | |
| 4,753,520 A | 6/1988 | Silverglate | |
| 6,144,455 A * | 11/2000 | Tuunanen et al. | 356/402 |
| 6,369,893 B1 | 4/2002 | Christel et al. | |
| 6,532,094 B1 | 3/2003 | Suhara | |
| 2001/0019114 A1 | 9/2001 | Arakawa et al. | |
| 2002/0109844 A1 | 8/2002 | Christel et al. | |
| 2002/0154289 A1 | 10/2002 | Wilks, Jr. | |

* cited by examiner

*Primary Examiner*—F. L. Evans
(74) *Attorney, Agent, or Firm*—Peter J. Dehlinger; Perkins Coie LLP (57) ABSTRACT

A diagnostics apparatus for detecting fluorescence events related to the presence of an analyte in a sample is disclosed. The apparatus includes a housing, a source of excitation light and a photodetector, and a unitary multi-surface optical module. The optical module is integrally formed and composed of an upstream portion having a focusing optical surface for directing excitation light from the light source to a focal region within an analyte-detection zone in the apparatus, and a downstream portion having a second focusing powered optical surface and at least one reflecting surface for directing fluorescence-emission light produced by fluorescence events within the detection zone, in a direction substantially normal to the path of the excitation light onto the photodetector. The optical module is adaptable to a variety of assay formats, including multiple-sample, sample-array, and disposable-cartridge formats.

25 Claims, 11 Drawing Sheets

MULTILENS OPTICAL ASSEMBLY FOR A DIAGNOSTIC DEVICE

This application is a continuation-in-part of U.S. patent application Ser. No. 10/705,162 filed on Nov. 6, 2003 now U.S. Pat. No. 6,929,945, which claims the benefit of U.S. provisional patent application No. 60/511,798 filed on Oct. 16, 2003, now abandoned, both of which are incorporated herein by reference in their entirety.

FIELD OF THE INVENTION

The present invention relates to a multilens optical assembly for use in a fluorescence-detection diagnostic device, such as a microfluidics diagnostic device, immunosorbent assay or gene chip, and preferably, to such an assembly formed as a unitary, i.e., single-piece polymer structure, e.g., by injection molding.

BACKGROUND OF THE INVENTION

There are many types of diagnostics devices that use optical sensing, such as fluorescence or absorption, to detect the presence or amount of analyte in a sample, e.g., blood, urine, or saliva sample. Fluorescence detection, in particular, has been adapted to many different types of enzyme, antigen, antibody, metabolite, nucleic acid and cell-type assays because of the high sensitivity and wide availability of fluorescent probes, and the different types of assay formats which are well-adapted to fluorescent probes.

As examples, gene chips or protein chips for detecting analyte binding to one or more array regions on a chip typically employ fluorescent markers to detect analyte binding to the chip. Antigen-analyte binding events are easily measured in a solid-phase or homogeneous assay format that employs fluorescent probes. Fluorescence detection based on proximity effects that rely of fluorescence quenching provides another major area of diagnostics and detection that take advantage of fluorescence properties.

One limitation of fluorescence-detection assay, however, has been the need for special fluorescence readers. Although such readers may not be expensive, they have prevented widespread adoption of fluorescence assays in home-testing and in small-clinic medical or veterinary settings, and in other medical or field diagnostic applications, e.g., in the testing of air or water for bioagents, that would benefit from small, easily portable and/or disposable assay equipment.

It would therefore be useful to provide a diagnostics fluorescence-detection apparatus or device that is designed for home or small-clinic use, and which can be easily adapted to a disposable test unit or disposable assay cartridge. It would be further desirable to provide such a device capable of handling multiple samples and/or sample arrays, such as nucleic acids arrays.

SUMMARY OF THE INVENTION

The application includes, in one aspect, a diagnostics apparatus for detecting fluorescence events related to the presence of an analyte in a sample applied to the apparatus. The apparatus includes a housing, a source of excitation light and a photodetector mounted in the housing, and an optical module incorporating multiple optical surfaces, carried in the housing, adjacent the light source and photodetector. The optical module is preferably formed as single-piece or unitary article, e.g., molded polymer article, and is composed of an upstream portion having a first focusing optical surface for directing excitation light from the light source to a focal region defining an analyte-detection zone in the apparatus, and a downstream portion incorporating a second focusing optical surface and at least one reflecting surface for directing fluorescence-emission light rays produced by fluorescence events within the detection zone, in a propagation direction substantially normal to the path of the excitation light energy within the detection zone, onto the photodetector.

An electronic unit in the housing is operatively coupled to excitation light source for activating the same, to the photodetector for receiving electronic signals therefrom, and for converting said signals to an analyte-detection signal, and to a display in the apparatus for displaying the detection signal.

In one general embodiment, the analyte-detection zone is positioned for receiving focused light energy from the fluorescence-excitation light source directly through an upstream focusing optical surface. In this embodiment, also referred to herein as a "direct-source" format, the light source may be a single LED, or two or more side-by side LEDS, for directing different wavelength excitation light a single focal region of the detection zone, or two or more separated focal regions within the detection zone.

Also in this embodiment, the optical module may have back and top faces and first and second reflecting surfaces formed on the back and top faces, respectively, for directing light from the detection zone to the second focusing optical surface in the module. The apparatus may include two or more side-by-side photodetectors for detecting separate, different wavelength fluorescence emission events within the detector. The focusing optical surface in the downstream subassembly may be of split (i.e., bifurcated), designed to direct fluorescence emission light from the detection zone to each of the photodetectors, through separate filters associated with each photodetector. Alternatively, the top face in the assembly may be of "roof" form, or may be curved to direct the fluorescence emission light from the detection zone into two or more side-by-side photodetectors.

The light source and photodetector may be carried on a support in the housing, with the optical module being mounted on said support. The detection zone in the apparatus may be contained in a sample-handling device designed for receiving a sample and directing the same into the detection zone.

The sample-handling device may include a microfluidics plate that is laminated to a surface of the optical assembly. Alternatively, the sample-handling device could be a strip that is inserted into the device assembly, such as a strip coated with solid-state chemicals that tag certain analytes with antibodies. The optical module, LED and photodetector components, and attached sample-handling device may form a disposable cartridge that is removably mounted in the housing.

The module may be formed as part of a plurality of such modules, arranged side-by-side, for detecting fluorescence events related to the presence of an analyte in a plurality of samples in a sample array. Alternatively, a single apparatus may includes a plurality of light-path sections, each for directing light from one of a plurality of light sources through an individual detection zone, e.g., in a linear array of detection zones, and from the detection zone to an associated photodetector.

In a second general embodiment, the light source and photodetector are oriented in substantially the same direction, and are disposed on opposite sides of the detection zone, such that light propagation path from the light source must be reflected as well as focused onto the detection zone, thus defining a "reflected-source" format. The detection zone may be part of a sample-handling device for receiving a sample and directing the same into the detection zone. The sample-handling device and optical module may be sealed together to form a cartridge that defines an enclosed fluid-handling structure having a sample-receiving well and an analyte-detection zone.

Also in the second general embodiment, the light source and photodetector may be oriented in substantially the same direction, and disposed on opposite sides of the detection zone. Here the upstream portion may include a first converging optical surface whose focal point is positioned at or near said light source, a second converging optical surface whose function is to focus excitation light from the first converging optical surface within the analyte-detection zone, and a first reflecting surface which cooperates with the second optical surface to reverse the direction of light rays between the light source and photodetector. The downstream portion may include a third converging optical surface whose focal point is positioned at or near the detection zone, and whose optical axis is substantially orthogonal to the optical axis of the second converging optical surface, a fourth converging optical surface effective to focus fluorescence light rays produced in the detection zone and passed through the third converging optical surface onto the photodetector, and second and third reflecting surfaces which cooperate with the third optical surface to reverse the direction of propagation of the emission light between the third optical surface and photodetector.

In all of these embodiments, the light source is preferably a light-emitting diode (LED), and preferably one that emits a desired fluorescence excitation wavelength, e.g., in the blue or green. The first optical surface encountered by the excitation light from the LED may have a curvature that acts to offset light rays from the diode toward the center of the optical field formed by the first optical surface, to enhance the brightness of the center region of the optical field.

The optical module described above, including the various embodiments noted, also forms another aspect of the invention.

These and other objects and features of the invention will become more fully apparent when the following detailed description of the invention is read in conjunction with the accompanying drawings.

BRIEF DESCRIPTION OF THE DRAWINGS

FIG. 6 is a flow diagram of operations carried out by the control unit in the device of FIG. 1, FIGS. 7A and 7B are perspective views of an optical module in the present invention, formed in accordance with a second general embodiment of the invention having a direct-source format, and showing light propagation paths for excitation and emitted (signal) light;

DETAILED DESCRIPTION OF THE INVENTION

The present invention includes a multisurface optical module in a fluorescence-detection diagnostics device or apparatus. As will be described below, the optical module is preferably formed as a unitary (single-piece) molded article, e.g., molded plastic article, and can be tailored to a variety of assay devices and formats, such as a microfluidics format, a multiple-sample format, and an array format. It can be manufactured to small dimensions, e.g., for use in a microfluidics or other small device, and can be integrated with sample-handling elements, e.g., by laminating a microfluidics plate to one of the assembly surfaces. The module, including attached fluid-handling structure, may be a disposable cartridge that can be removably inserted into a reader apparatus, or may be a fixed element of a disposable device.

In its most general aspect, the optical module includes (i) an upstream portion having a first focusing optical surface for directing excitation light from a light source to a focal region defining an analyte-detection zone, and (ii) a downstream portion having a second focusing optical surface and at least one reflecting surface for directing fluorescence-emission light produced by fluorescence events within the detection zone, in a direction substantially normal to the path of the excitation light rays within the detection zone, onto the photodetector.

For purposes of illustration, the optical module will be described with respect to two general embodiments. One embodiment has a "reflected-source" format in which light from the fluorescence-detection source must be reflected as well as focused onto the detection zone. A reflected-source embodiment of an optical module is illustrated below in FIG. 2, and is described as part of a disposable sperm motility diagnostic apparatus designed to measure sperm count and motility, based on the accumulation of fluorescent signal (from fluorescent-labeled sperm) in a microfluidics reservoir chamber. More generally, this embodiment is suitable for any fluorescence-detection device having an offset light-source/detection-zone configuration.

In another general embodiment, described with respect to FIGS. 7–12, the analyte-detection zone is positioned for receiving focused light from the fluorescence-excitation light source directly through an upstream focusing optical surface. In this embodiment, also referred to herein as a "direct-source" format, the light source may be a single LED, or two or more side-by side LEDS, for directing different wavelength excitation light into a single or one or more focal regions therein.

The direct-source format simplifies the optical design of the module, as will be seen. This embodiment is suitable for any fluorescence-detection device in which excitation light from one or more light sources is focused directly (without reflection) at one or more focal regions within a sample holder. For example, in an array format, the optical module may incorporate an optical surface array for focusing light from a single source onto each of a plurality of array detection zones.

A. Assay Apparatus with Reflected-Source Format

Figure 1:
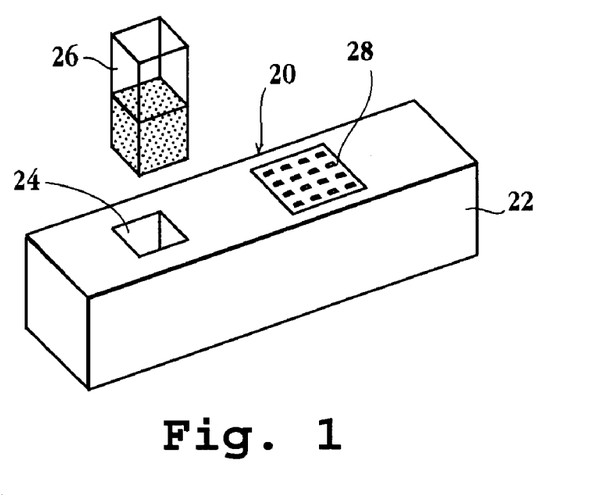
FIG. 1 shows, in perspective view, a disposable assay apparatus constructed according to one embodiment of the invention.

FIG. 1 illustrates a self-contained assay apparatus or device 20 constructed in accordance with the present invention, for measuring sperm motility in a forward direction and density of active sperm in a semen. Shown in the figure is an outer case or housing 22 which houses (i) internal sample-handling structure within which sperm motility characteristics will be determined, (ii) a detection system including a light source and a photodetector for detecting fluorescence events, in this case, the accumulation of fluorescent-labeled sperm within the microfluidics structure, (iii) a multi-surface optical module, and (iv) electronics control unit operatively connected to the detection system, for determining sperm characteristics based on detected signals. The construction and operation of these components will be discussed below.

As seen in FIG. 1, the case 22 defines a sample-receiving opening 24 that communicates internally with a sample-receiving reservoir in the microfluidics system in the device, as will be described. Also shown is a cuvette or sample-collection holder 26 for collecting the total ejaculated semen volume, and sample preparation. The cuvette may indicate with a volume-indicator marking (not shown) the minimum semen volume, e.g., the 1.5 mL volume determined necessary by the WHO standards for adequate male fertility. The cuvette may be directly inserted into opening 24 of the device, for transferring fluid from the holder to the microfluidics structure in the device, or an additional sample-preparation vessel may be provided to contain a smaller volume of the total ejaculate semen volume, a dilution of the total sample, or a mixture of the total sample with other liquid or solid chemicals.

The cuvette to be inserted into the sample-receiving well is called the aggregate sample holder and may have a bottom aperture consisting of the entire bottom face of the cuvette, or some smaller geometry set within the bottom face that is readily perforated by a sharpen access (such as a syringe needle) port in the bottom of the opening. The bottom face may be made of rubber or wax to allow perforation without leakage of the sample. The sample may be drawn into the fluidic pathway by capillary action. The sample holder may be pre-loaded or coated with solid and/or liquid chemical compounds, such as a labeling compound and/or digestive enzymes. Digestive enzymes such as collagenase or trypsin may be used to facilitate the natural proteolytic breakdown of the semen sample. Chemicals such as sodium chloride and fructose may be added to increase the in vitro survivability of the semen sample. The cuvette also typically includes a sperm labeling reagent for labeling sperm with a detectable reporter, such as a fluorescent reporter, as discussed below.

The sample holder may be either prefilled with liquid reagents, or these may be supplied to the user in a separate fluid dispenser for addition to the sample in the holder. The liquid reagents may include an iso-osmolar (approximately 290 mOsm) solution of sugar and salt in water, consisting primarily of but not limited to fructose, sodium chloride, calcium chloride, magnesium chloride, and potassium chloride, maintained at physiological pH by HEPES buffering.

The pre-filled solution or solid reagent in the holder may contain a labeling compound, or the labeling compound may be included in solid form in a loading reservoir or in the graduated cylinder. The labeling compound will be weakly fluorescent in solution, either because of concentration or quantum yield, and highly fluorescent on or in the sperm cell, either because of increased concentration due to active accumulation, partition, or esterase activity, or because of increase in quantum yield because of lipid insertion or change in environment.

Once the sample holder is inserted into the device, a sharpened access port is used to pierce the bottom of the aggregate sample holder and the aggregate sample thereby gains access to the fluid pathway within the assay device. Alternatively, the sample, once mixed with the reagents in the cuvette may be poured into the opening, and from there enter the microfluidics structure, e.g., by dissolving an enzyme-dissolvable plug or following removal of a seal by the user. Also shown in the figure is a display 28 for displaying assay results to the user. Device 20 is manufactured, in a preferred embodiment, as a small, hand-held, disposable device.

Figure 2:
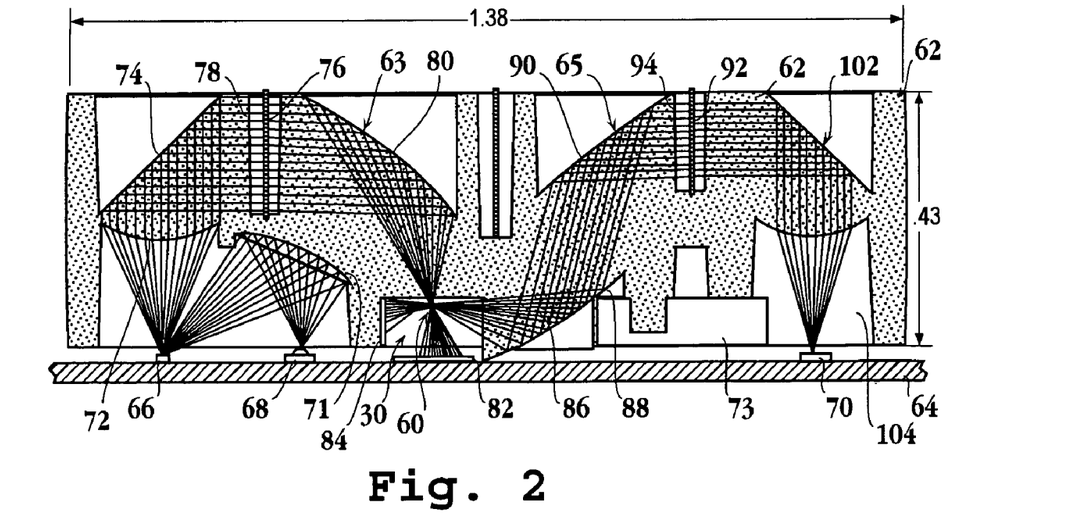
FIG. 2 is a sectional view of a unitary optical module having a reflected-source format, and shown here with other components in the apparatus of FIG. 1, including a microfluidics device providing an analyte-detection region, and an LED light source and a pair of photodetectors carried on a support in the apparatus.

As described below with respect to FIGS. 1–6, the device has an in-plane format in which an LED light source, the analyte-detection zone, and photodetector are all carried on a support, substantially in the same plane. FIG. 2 shows internal components of device 20, including microfluidics sample handling structure 30 having a collection chamber which contains a detection zone defined by a focal region 60 in the device, a light-emitting diode (LED) light source 66, pair of photodetectors 68, 70, and a multi-surface optical module 62 constructed in accordance with the invention. All of these components are mounted on a support or plate 64.

The optical module generally includes an upstream portion 63 for directing excitation light (indicated by dark lines) from LED 66 to a focal region 60 within the collection chamber, and a downstream portion 65 for directing fluorescence-emission light (indicated by lighter lines) produced by fluorescence events within the detection zone, in a direction substantially normal to the path of the excitation light within the detection zone, onto photodetector 70.

Considering details of the assembly, and with continued reference to FIG. 2, divergent light from LED 66 is reflected from curved reflecting surface 71 and focused onto detector 68. The light intensity measured at this detector is used to calibrate LED light intensity, relative to light intensity measured at detector 70 resulting from fluorescence emission produced within the detection zone. Divergent light from the LED is also directed through an optical surface 72, producing a beam of collimated light, as indicated. This light is reflected from a right-angle reflecting surface 74, and the reflected beam is then passed through a band-pass filter 76 contained in a filter inset 78 in the device. Filter 76 is designed to remove low frequency components produced by the LED, e.g., red and green components that are likely to have overlap with fluorescence emission wavelengths. One preferred filter is a 470–490 nm (blue) bandpass filter. The reflected, filtered light is again reflected by means of a concave reflecting surface 80, which serves to focus the reflected light into collection reservoir 60 in the microfluidics structure. The intensity of excitation light in the sample reservoir may be further enhanced by a reflector 82 positioned below the reservoir on plate 64.

As can be appreciated from the propagation path diagrams in FIG. 2, the above-described paths of the excitation light confines the propagation paths along the directions that are substantially in the vertical direction in the figure. In order to minimize overlap between excitation and emitted light, fluorescence emission is detected by collecting emission light of light directed is substantially orthogonal to the path of the excitation light, that is, in a substantially horizontal direction in the figure. This emitted light is either passed directly into an optical surface 86 in the optical module or reflected into this surface by a passive reflector 84 located on the opposite side of the collection reservoir. Emitted light directed into element 86 is internally reflected by a curved reflecting surface 88 to an oblique-angle reflector 90, and then passed through a filter 92 contained in a filter insert 94. The filter is a band-pass filter designed to remove light frequencies above fluorescence emission wavelengths, representing excitation frequencies from the LED. One preferred filter is a 505–540 nm (green) bandpass filter. The filtered emission beam is reflected from right-angle reflecting surface 102, and focused on passing through converging optical surface 104 onto detector 70, which then measures intensity of fluorescence emission from sample material in the collection reservoir.

The features of the optical module are preferably formed as functional aspects of a single molded plastic part, implemented in polystyrene, polycarbonate, polymethylmethacrylate, or other polymers having a relatively high index of refraction and good optical transmission. In the particular embodiment shown, the entire assembly is formed from a single polymer material, although in other embodiments, polymers with different indices of refraction may be employed. The reflecting surfaces on the plate 64 are formed by applying an adhesive tape with a reflective coating, or by applying a reflective metal coating with vapor or plasma deposition methods. Reflections within the optical module may be accomplished by total internal reflection (TIR), provided the refractive index of the polymeric material is sufficiently high. Otherwise, reflective coatings could be used.

Figure 3A:
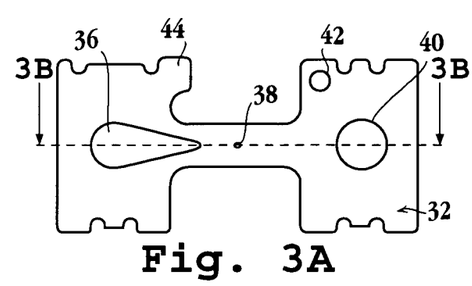
FIGS. 3A–3F show (3A) a plan view of the bottom plate in the microfluidics device shown in side view in FIG. 2, (3B) a sectional view through line A—A in FIG. 3A showing a central detection reservoir and wells for connecting the input ports to the microchannel, (3C), a plan view of the top plate in the microfluidics assembly, (3D), detail of end regions of a microfluidics channel and opposing reservoirs formed in the top plate; and (3E) detail of microfluidic channel and reservoir outline formed in the top plate; and (3F) the full assembly with the top and bottom plates stacked.
Figure 3B:
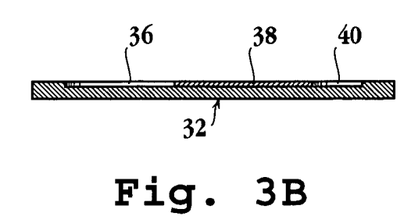
Figure 3C:
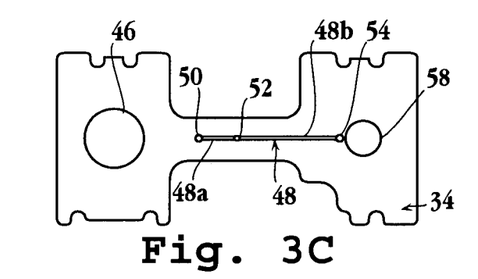
Figure 3D:
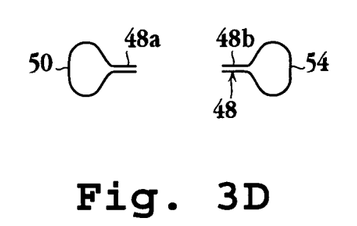
Figure 3E:
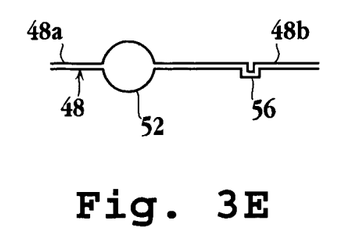
Figure 3F:
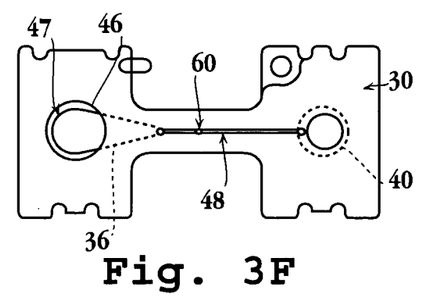

The construction of sample-handling structure 30 is detailed in FIGS. 3A–3F. As seen in FIG. 3F, a structure 30 is a microfluidics device formed of a bottom plate 32 (FIG. 3A) bonded to an aligned top plate 34 (FIG. 3C). As seen best in FIGS. 3A and 3B, bottom plate 32 includes a tear-drop shaped recess 36 formed in its upper surface, at the upstream end region of the plate, a central cylindrical reservoir recess 38, which will form part of a collection reservoir in the structure, and a downstream recess 40. Also formed in the lower plate is a circular alignment recess 42 used in aligning the lower and upper plates when the two are bonded together, and a tab 44 used in aligning an optical element on structure 30, as will be seen.

Considering now the construction of top plate 34, and with reference to FIGS. 3C–3E, a sample-receiving opening 46 is formed at the upstream end of the plate. A microfluidics channel 48 formed in the lower side of the plate has two separate channel segments: an upstream segment 48a extending from an upstream feed recess 50 to a central reservoir recess 52, and a downstream segment 48 extending recess 52 to a downstream drain recess 54. Recesses 50, 54, and adjoining portions of channel segments 48a, 48b, respectively, are shown in enlarged view in FIG. 3D. Recess 52 (seen in enlarged view in FIG. 3E) has the same circular dimensions as reservoir recess 38 in the bottom plate, and forms therewith, in the assembled structure, a cylindrical collection reservoir 60 (FIG. 3F) in which labeled sperm will collect for detection, as discussed below. In an exemplary embodiment, the collection reservoir has a cylindrical radius of between 0.1 and 1 mm, and a depth of between 0.1 and 1 mm, to produce a known volume of between 0.001 and 1 mm$^3$.

Just downstream of recess 52, in channel segment 48b, is a channel detour 56 (FIG. 3E) which functions to limit flow of motile sperm downstream of the detour, acting thereby to limit the movement of motile sperm beyond the reservoir.

As noted above, the microchannel in this embodiment, meaning the two microchannel segments 48a, 48b, have width and depth dimensions each between about 10–100 microns, preferably in the range 15–60 microns. The microchannel may be of any convenient cross-sectional geometry, such as semi circular or rectangular, and might be up to several cms in length. Functionally, the microchannel, and in particularly, microchannel segment 48a, is dimensioned to allow motile sperm to advance through the channel in an upstream to downstream direction, but within a sufficiently confined space that the sperm have a very low probability of reversing their direction of movement within the channel. As will be seen below, the channel width and/or depth may accommodate sperm moving through the channel side by side or may confine the sperm to single-file motion. In the former case, channel width and depth dimensions are preferably between 50 microns and 100 microns; in the latter, between 10 and 30 microns.

As can be appreciated from the forgoing descriptions of plates 32, 34, and from FIG. 3F, the assembled structure has a sample inlet port formed by opening 46, and this port communicates with recess 36 in the lower plate to form a sample-receiving station 47. At its downstream end, recess 36 overlaps with upstream feed recess 50 in the upper plate, for capillary transfer of liquid from recess 36 into recess 50 and from this recess into microchannel 48, where the central region of the microchannel is interrupted by cylindrical collection reservoir 60. From this reservoir, fluid is drawn from the down microchannel 48b to recess 54, which overlaps recess 40, acting to distribute liquid in a drain reservoir formed by recess 40 and opening 40. The fluid pathway just described in structure 30 is typically filled with a suitable liquid medium, e.g., isotonic salt solution, in manufacture, and sealed prior to use. When sample fluid is added to the device, the sample mixes with the preloaded fluid in the sample-receiving station. Sperm contained in the sample, and now in the sample-receiving station, become quickly distributed throughout this station, initiating the series of sperm-migration events that will form the basis for determining sperm motility and density of forward-moving sperm, as described below.

Plates 32, 34 may be fabricated using injection molding of polymer material, preferably transparent polymer such as polypropylene, polycarbonate, or any other optically transparent polymer which is known to provide well-defined and stable molded features. Alternatively, the plates may be formed by well-known surface fabrication methods applied to any of a variety of suitable materials, such as silicon, glass, quartz, plastic, or other polymer. In the latter approach, the channels may be made by laser ablation or chemical etching. Channels of the size proposed can be achieved by focusing the laser used in ablation or by using microlithography to mask the substrate before etching. These processes can also be used to make the masters/moulds used for injection molding. Each plate has typical width, length, and thickness dimensions of between 0.5 to 2 cm, 2–4 cm, and 1–2 mm. Total thickness of the assembled structure is typically 2–3.5 mm. Recess thickness dimensions, other than for recess 52, are typically 25 to 100 microns. The two plates, once formed and placed into alignment with one another, are bonded by conventional methods, e.g., chemically, electrostatically, or through heat and pressure (fusion bonding).

The photodetector in the assay apparatus may be a photodiode, charge-coupled-device (CCD), or other solid-state detector. These devices are inexpensive, reliable, have a fast time-response, and available in a wide range of wavelength sensitivity profiles and sizes. An exemplary LED is a UNPRX465-0G1 LED supplied by Uniroyal, which emits light primarily in the blue wavelength around 465–470 nm. An exemplary photodetector is an OSD1-0 photodiode supplied by Centronic.

As can be appreciated from FIG. 3, the optical module straddles the center "cut-out" portions of the microfluidics structure, and is aligned therewith by a suitable means between the optical element and a tab or tabs in structure 30. The optical element is further aligned on plate 64 by interdigitation with a mounting block 72 carried on plate 64, or through having hole in plate 64, which align to pegs on the optical module.

Figure 4A:
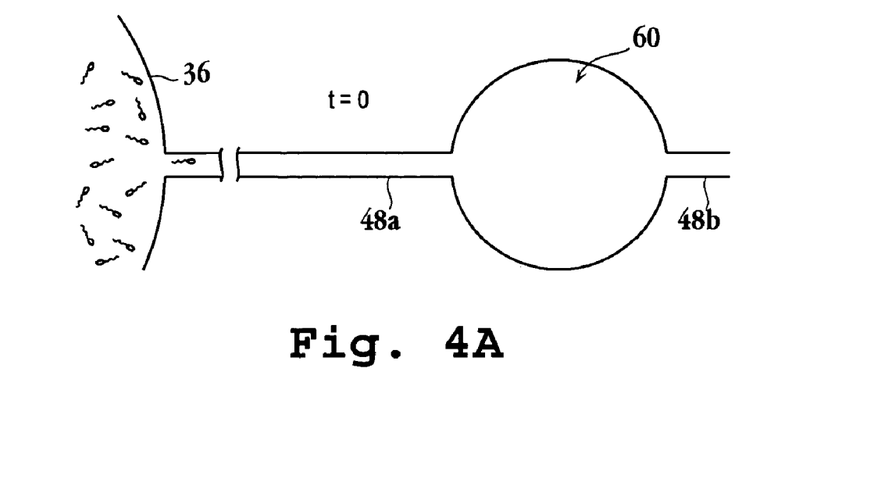
FIGS. 4A–4C illustrate conditions of sample movement and distribution during operation of the apparatus in FIG. 1, at three different time points.
Figure 4B:
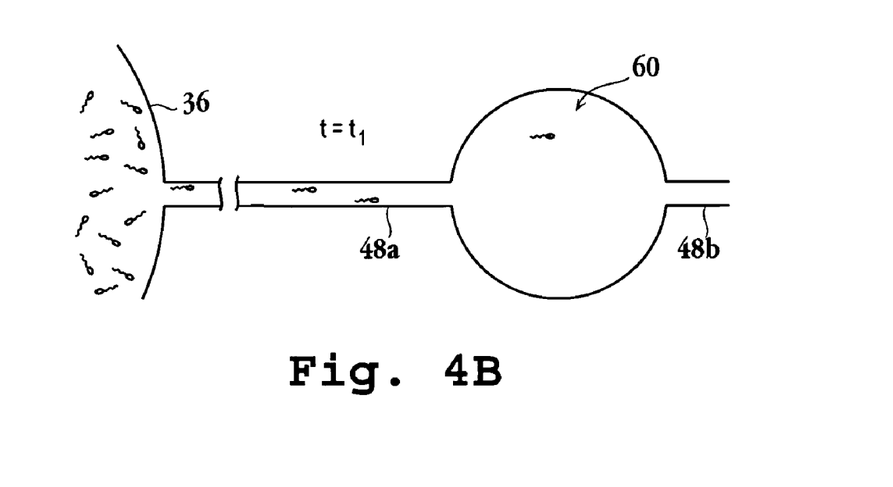
Figure 4C:
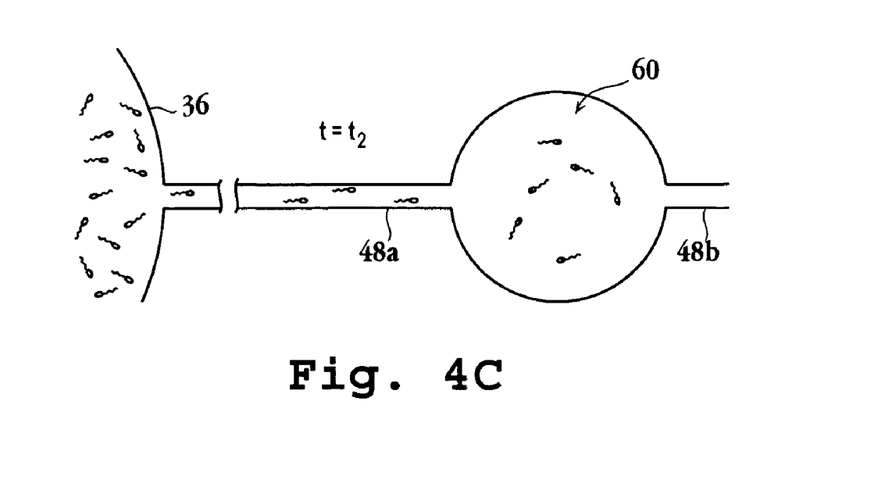

The dynamics of sperm motility that allows for quantitation of sperm motility and density of active sperm is illustrated in FIGS. 4A–4C. The figures show the microchannel portions of microfluidics structure 30, including the downstream end of feed recess 50, microchannel segment 48a, collection reservoir 60, and microchannel segment 48b. When pretreated semen sample is first introduced into the device, at time t=0, the labeled sperm cells in the sample quickly distribute through the fluid contained in the sample-receiving station. That is, microchannel segment 48a is virtually free of any labeled cells, as shown in FIG. 4A. Over time, e.g., at time t=$t_1$, motile, forward-moving sperm cells find their way into channel segment 48a, and begin migrating, at a migration rate dependent on the average motility of the cells, toward reservoir 60. As motile, forward-migrating cells complete their journey through channel segment 48a, they begin to accumulate in reservoir 60, leading to an increase in the fluorescence signal measured in the reservoir.

Figure 5:
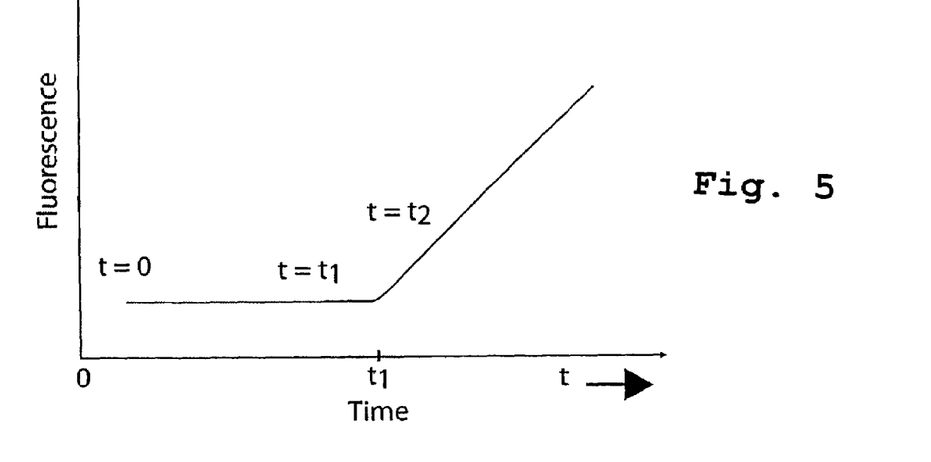
FIG. 5 shows a typical sperm-concentration function generated by the apparatus of FIG. 1 during an assay operation.

The above cell-migration events, as manifested in fluorescence detection within the reservoir over time are plotted in FIG. 5. At time t=0, measured fluorescence is at some low, background level, and remains so up till time $t_1$, when labeled cells first begin to reach the reservoir. As more and more labeled cells begin to accumulate in the reservoir, the total measured fluorescence begin to rise, in this figure, showing a linear rise over time past $t_1$. with a slope of change in fluorescence/given time period. By extrapolating the slope back to a zero-slope time, ($t_1$), the time $t_1$ required for migration of sperm cells through channel segment 48b can be determined.

The electronic components of the device include a microprocessor and powered with a small battery. The detector signals are digitized by an AD converter or comparator and then stored in the microprocessor's RAM. The microprocessor then computes the density and motility according to the logic described below. The design and construction of the microprocessor will be evident to one skilled in the art, in view of the output and logical operations now to be described.

Figure 6:
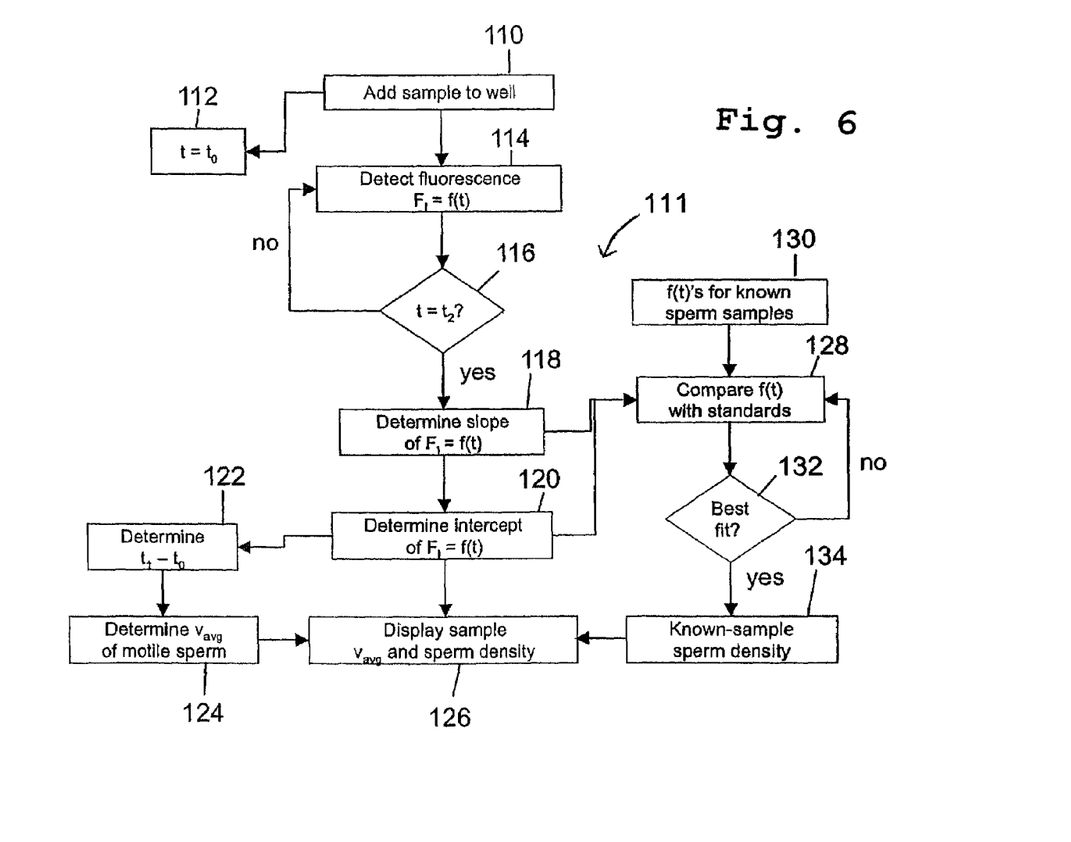

The steps performed by the device microprocessor, indicated generally at 111 in FIG. 6, in carrying out these assay determinations, is shown in flow diagram in FIG. 6. When sample is first added to the device, as at box 110, a signal is sent, e.g., by sample fluid closing a conductive pathway between two electrodes, to the microprocessor, setting a clock time to 0, as at 112. Activation may also be done manually through a switch or by connecting a sensor to a foil or plug structure that is covering the sample well. When the protective cover is removed the sample is activated. At the same time LED 66 is switched on, and the microprocessor begins to receive time-dependent fluorescence emission signals from detectors 68 and 70.

Optical detection is continued for a preset time $t_2$ that is long enough to record a reliable plot of increased fluorescence in reservoir 60. When this time is reached, through logic 116, the processor analyzes the fluorescence curve to determine a slope of the time-dependent fluorescence curve, using a standard curve analysis algorithm, as indicated at 118. From this curve, a "zero intercept" where the slope intersects the horizontal baseline is determined, at 120, and from this, the average time of travel of active sperm through channel segment 48a ($t_1-t_0$) and an average velocity of motile sperm are determined at 122, 124, respectively. That is, from the known average time of travel, and the known length of channel segment 48b, the rate of migration of motile cells in a forward direction moving cells within the channel can be calculated (rate=distance/time $t_1$). The calculated velocity, or a qualitative indicator of sperm mobility, is displayed to the user at 126.

To determine density of motile sperm, the slope of the time-dependent curve determined at 118 and 120, is compared at 128 with each of a plurality of known slopes, each representing time-dependent fluorescence measurement taken under identical conditions with different known sperm samples, stored at 130. Although not shown in the figure, the slope of the fluorescence curve for sample is adjusted to a standardized excitation intensity to compensate for variations in actual LED excitation intensity, as measured as detector 68 in the device, so that the sample curve and all of the model curves are based on a standardized excitation value. Suitable methods for curve fitting and matching are well known in the art. Once a best curve fit is made, at 132, the density of motile sperm in the sample is estimated from the best-fit curve, and displayed to the user at 126.

B. Multilens Optical Assembly with Direct-Source Format

Figure 7A:
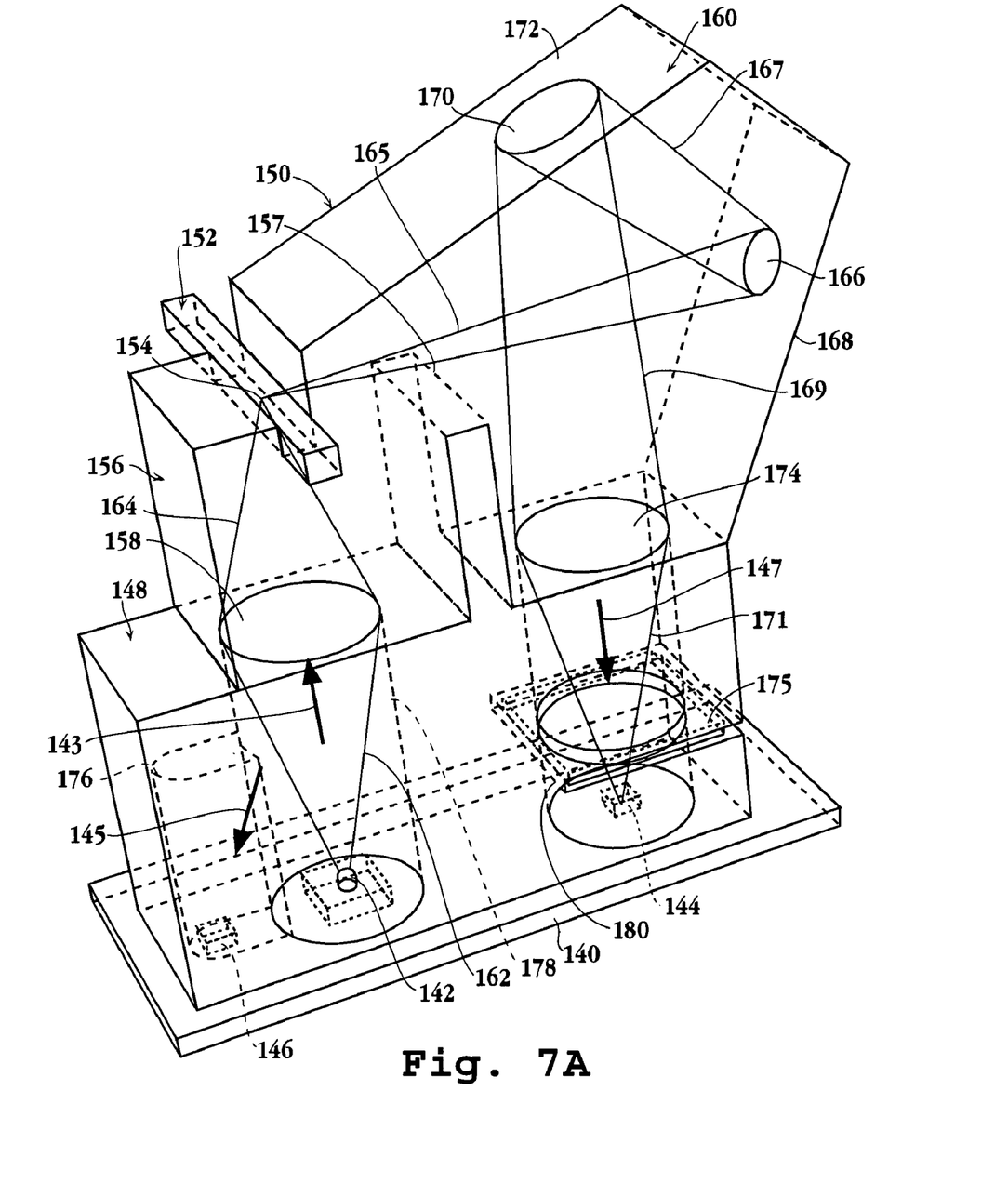
Figure 7B:
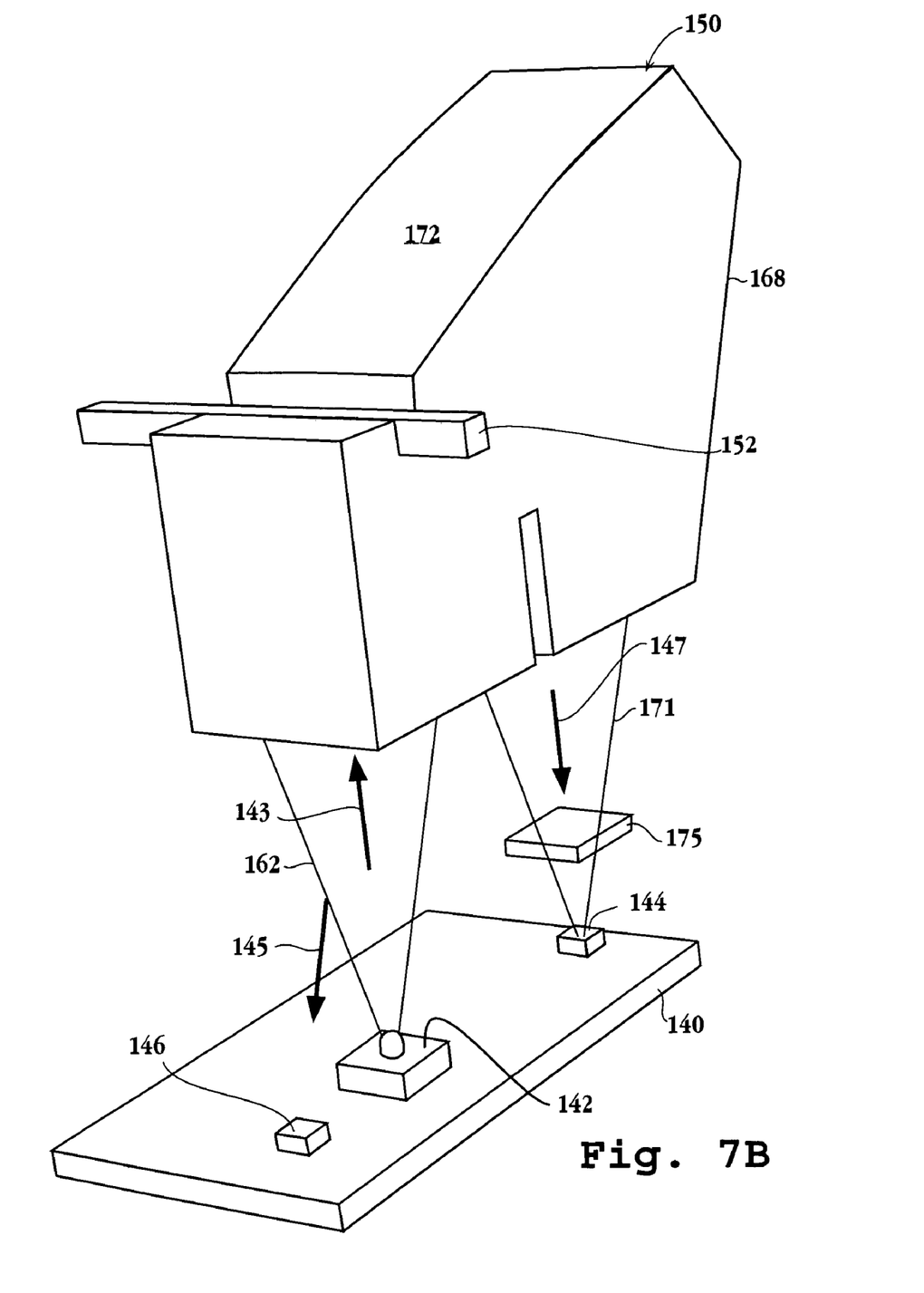

FIGS. 7A and 7B shows optical components in an assay apparatus constructed according to a second general embodiment of the invention having an optical module with a direct-source format. Shown in the figure are a support plate 140 supporting thereon an LED light source 142, a pair of photodetectors 144, 146, and a support block 148 (shown in FIG. 7A only) which in turn, supports an optical module 150 having a direct-source format. A sample holder 152 (FIG. 7A) formed on the optical module provides an analyte-detection zone at which fluorescence detection events are produced by fluorescence excitation in the sample holder, and which is centered a focal point 154 in the sample holder. The focal point in the detection zone is located on a vertical axis extending through the center of LED 142.

Although not shown here, the apparatus of this embodiment also includes a housing with an external delay, sample-handling structure by which sample material is introduced into the apparatus and supplied to the sample holder, and a control unit which operates to activate the light source, receive signals from the photodetectors, and determine the presence or amount of an analyte, from the fluorescence detection signals received from photodetector 144. This unshown components may be substantially as described and illustrated with respect to apparatus 20, where the operation of the control unit will depend on the assay format, according to design principles well known to those of skill in the art.

Module 150, which is formed as a unitary or single molded plastic piece, generally includes an upstream portion 156 for focusing light from LED 142 within a focal region centered at focal point 154, defining a detection zone in the sample holder, and a downstream portion 160 for reflecting and focusing fluorescence emission light produced in the detection zone onto photodetector 144. A notched region 157 between the two subassemblies may be filled with an opaque material to shield the downstream portion from stray light from the LED.

The principal optical element in upstream portion 156 is a convex focusing optical surface 158 which "sees" a cone of light 162 from LED 142, and forms a cone of light 164 whose focal point is the focal region defining the detection zone in the sample holder. The optical surface 158 also acts to reflect some of the incident light from LED 142 back on photodetector 146, and the signal from this photodetector is used to calibrate the light intensity from LED 142, as described above in apparatus 20.

The downstream portion of module 150 includes, as its critical optical elements, a first reflecting surface 166 which "sees" a cone 165 of fluorescence emission light produced within the detection zone in a direction substantially normal to excitation beam, a second reflecting surface 170 which "sees" the reflected cone of light 167 from surface 166, and a focusing optical surface 174 which focuses the reflected cone of light 169 from surface 170 onto photodetector 144. Reflecting surfaces 166, 172 are formed as in the optical module by coating a portion of the back and front faces of the assembly, indicated at 168, 172, respectively, with reflective tape or a reflective metal coating. It will be understood that the elliptical reflection regions shown at 166 and 170 represent only those portions of the reflecting surfaces that contribute to the fluorescence-emission light rays that ultimately reach the photodetector. It will also be understood that reflectance may be by total internal reflectance (TIR), as described above.

Support 148 is a molded or machined bloc, preferably opaque, having internals spaces, such as shown at 176, 178, and 180, that accommodate the transfer of light between LED 142 and lens 158, indicated by arrow 143, between LED 142 and photodetector 146, indicated by arrow 145, and between lens 174 and photodetector 144, indicated by arrow 147.

Also shown in FIGS. 7A and 7B is a bandpass filter 175 for selectively filtering the excitation light to remove stray light from the LED.

Figure 8:
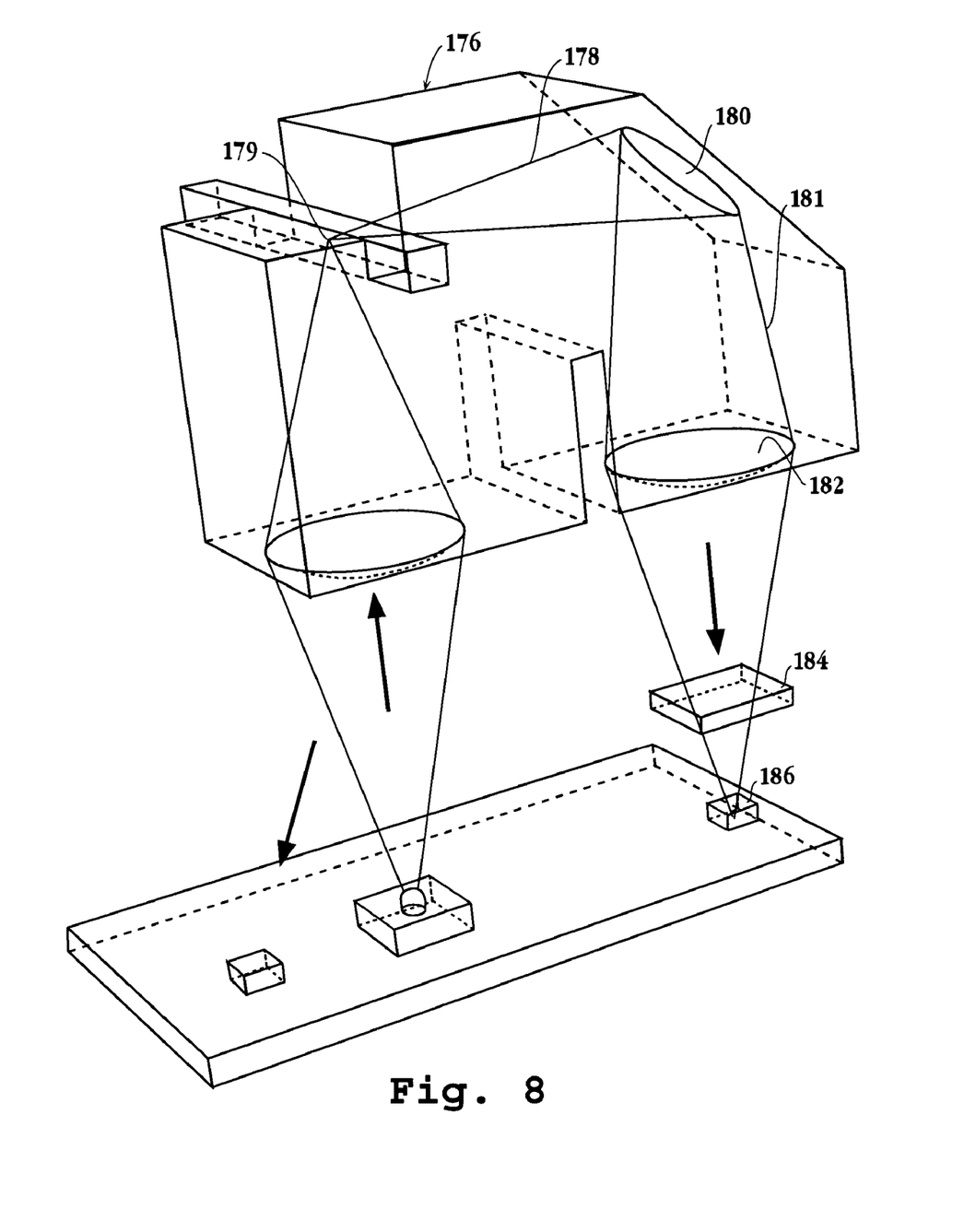
FIG. 8 is a perspective view of an optical module in the present invention, having a direct-source format, but different reflecting surface structures than in the embodiment illustrated in FIGS. 7A and 7B and in FIGS. 9–12.

FIG. 8 illustrates optical components in a diagnostics assay apparatus in which the optical assembly, shown at 176, has a direct-source format, but in which a cone 178 of fluorescence emission light from a detection zone 179 is reflected by a single reflecting surface 180, producing a cone of light 181 which is seen by a focusing optical surface 182, and focused onto a photodetector 186 through a filter 184.

Although the FIG. 8 embodiment has a simpler optical configuration than that shown in FIGS. 7A and 7B, the latter has two important advantages. First, the optical train involving reflection from two surfaces in the FIG. 7 embodiment is easier to construct in a molded form, due to its closer approximation in finished form to circular cross-section, since a more spherical shape or circular cross section in a molded article will reduce shape distortions resulting from unequal rates of cooling of the injected polymer. Secondly, the embodiment of FIGS. 7A and 7B is less sensitive to misalignment effects between the focused fluorescence emission beam and the photodetector, due to the longer path length and the narrower cone of sampled light provided by the two reflecting surfaces.

Figure 9:
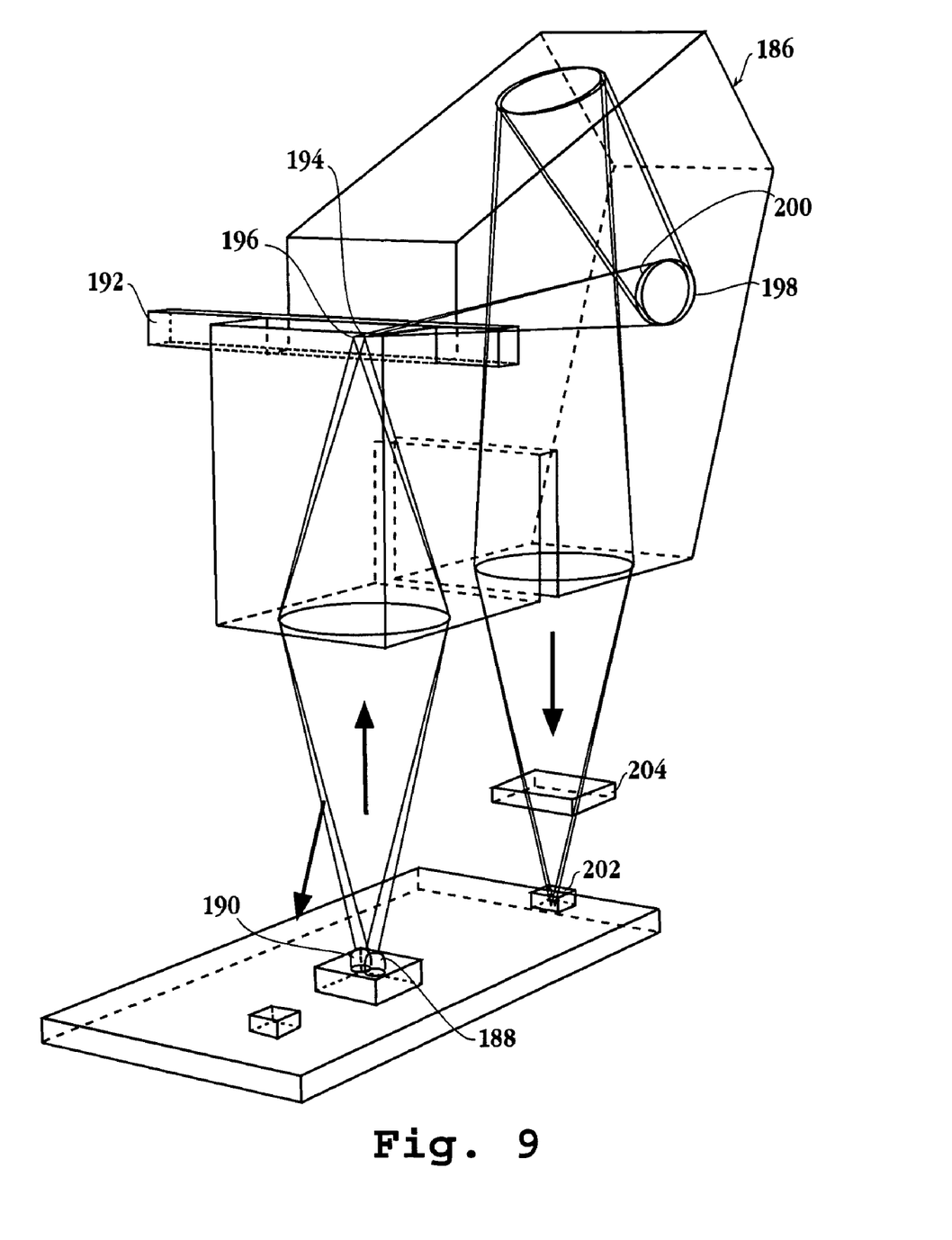
FIG. 9 is a perspective view of an optical module like that shown in FIG. 7, but where the apparatus includes two closely spaced LED light sources.

FIG. 9 illustrates an optical assembly 186 identical to that described with respect to FIGS. 7A and 7B, but used in an assay apparatus whose excitation light source includes two closely spaced LEDs 188, 190. The two LEDS have different excitation wavelengths, such as blue and green, either for exciting two different analyte-related species in sample holder 192, or for purposes of generating fluorescence emission readings from the same species at two different wavelengths, e.g., for purposes of eliminating non-analyte fluorescence-emission events. The spacing between the two LEDs is typically between about 0.1 and 1 mm, where each LED has a light emission area typically of about 0.05 mm$^2$.

As seen in FIG. 9, the cones of light from the two LEDS are focused at closely spaced analyte-detection zones 194, 196 in the sample holder, giving rise to closely matching fluorescence emission cones 198, 200 in the downstream subassembly. The light rays from these cones are focused onto substantially the same portion of the photodetector and are thus treated as equivalent rays for purposes of origin of the emission source. The control unit in the apparatus is designed to selectively activate and record fluorescence emission events at each wavelength separately. A band pass filter 204 may be used to filter stray light from one or both of the two LEDS, e.g., by combining two bandpass that selectively transmit the two different excitation wavelengths. Alternatively, the control unit may operate to move two different filters in and out of position, according to the LED activated at any time.

Figure 10:
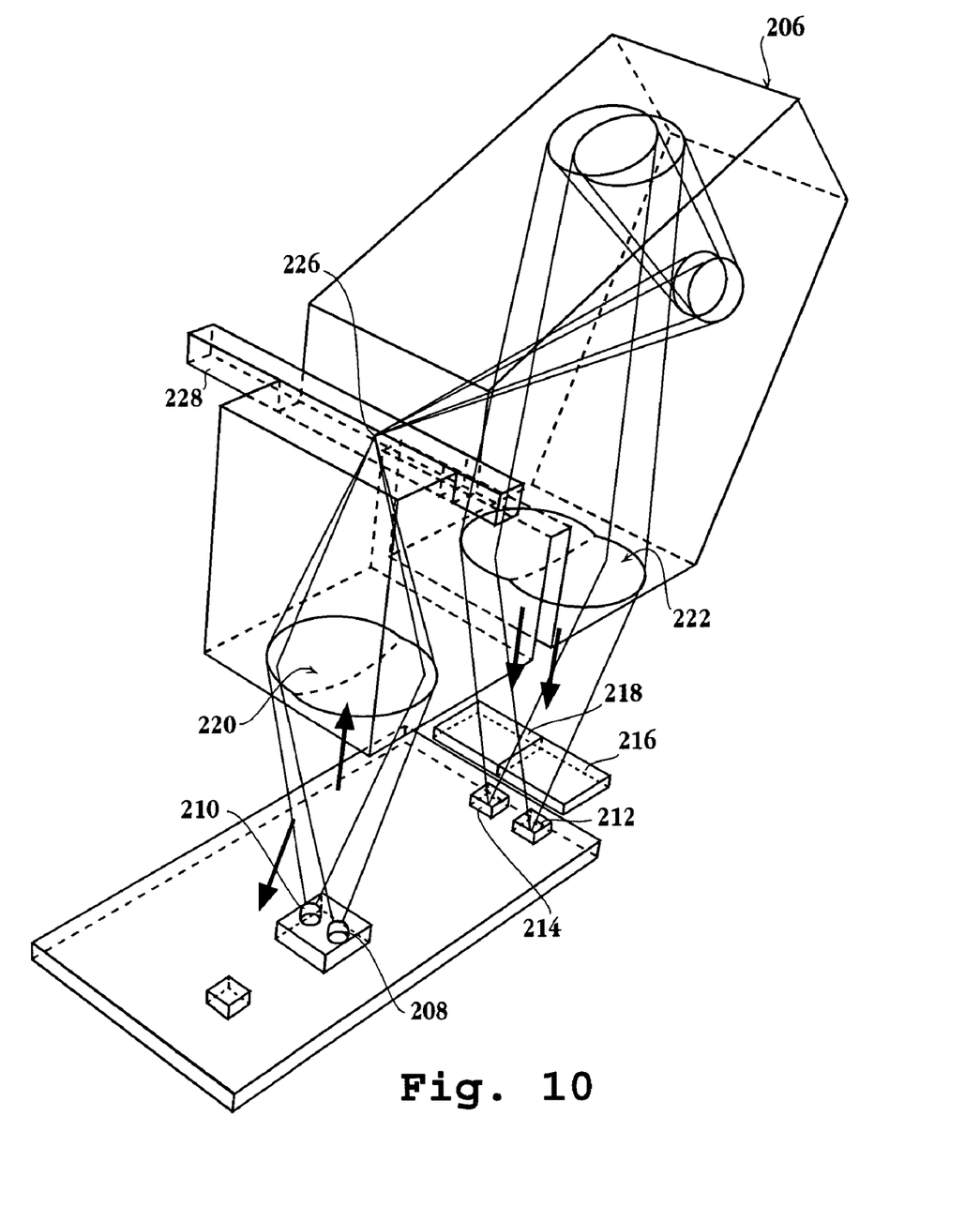
FIG. 10 is a perspective view of an optical module like that shown in FIG. 7, but where the apparatus includes two spaced LED light sources and two spaced photodetectors.

FIG. 10 illustrates an optical assembly 206 similar to that just described but modified for use in an assay apparatus having a pair of spaced LEDs 208, 210 (e.g., 480 nm, blue and 535 nm, green), and a corresponding pair of spaced photodetectors 212, 214 and associated band-pass filters 216, 218 (e.g., 505–540 nm, green and 580–630, red), respectively. In this embodiment, the focusing lens in the upstream subassembly, indicated at 220, is a split (bifurcated) lens designed to focus light from each of the two LEDs onto a single detection zone 266 in a sample holder 228. Fluorescence-emission light from the detection zone, in turn, is focused onto one of the two photodetectors, through a split lens 222. It will be appreciated that the split lens acts to focus fluorescence emission at both different wavelengths onto each of two photodetectors, and that filters 216, 218 function to selectively pass fluorescence emission excited by one of the two LEDs onto two photodetectors. Thus, each set of reflected light cones that are shown emanating from the detection zone, and focused onto one of the two detectors, represents the light ray cones that are seen by that photodetector, after filtering the focused light rays through one of the two band-pass filters.

It will be appreciated how the modules illustrated in FIGS. 7–10 can be adapted to a multiple-sample format. In one embodiment, a multiply split optical surface is designed to distribute light from each of a plurality of LEDs aligned along the axis of the excitation beam path, at each of a plurality of horizontally and vertically spaced sample zones. Excitation of sample in each zone produces a solid angle of light that is reflected onto a single photodetector or onto multiple spaced photodetectors, if a multiply split focusing surface is employed.

Figure 11:
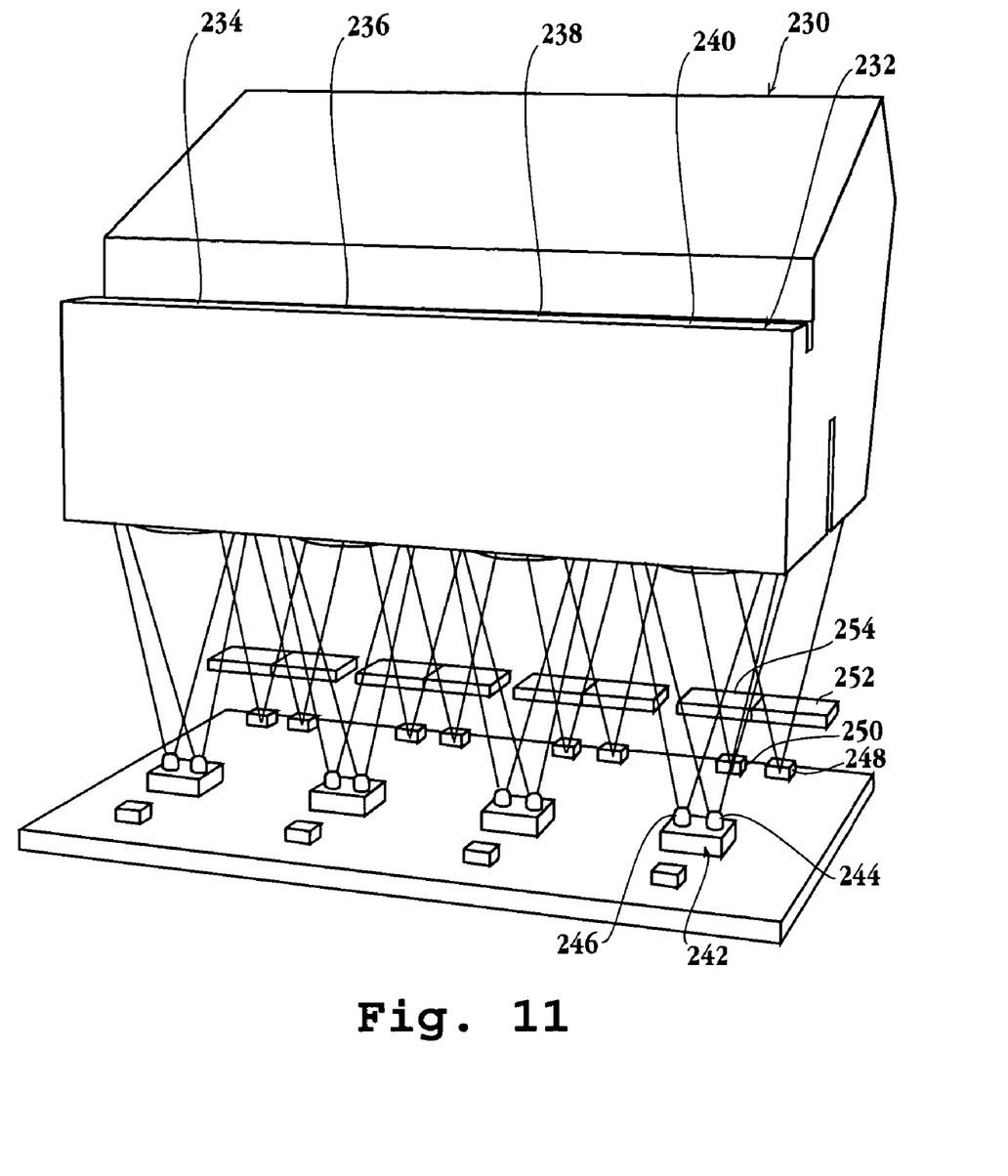
FIG. 11 is a perspective view of an integrated optical module designed to detect analyte in each of four chambers, and at each of two different excitation and emission wavelengths.
Figure 12:
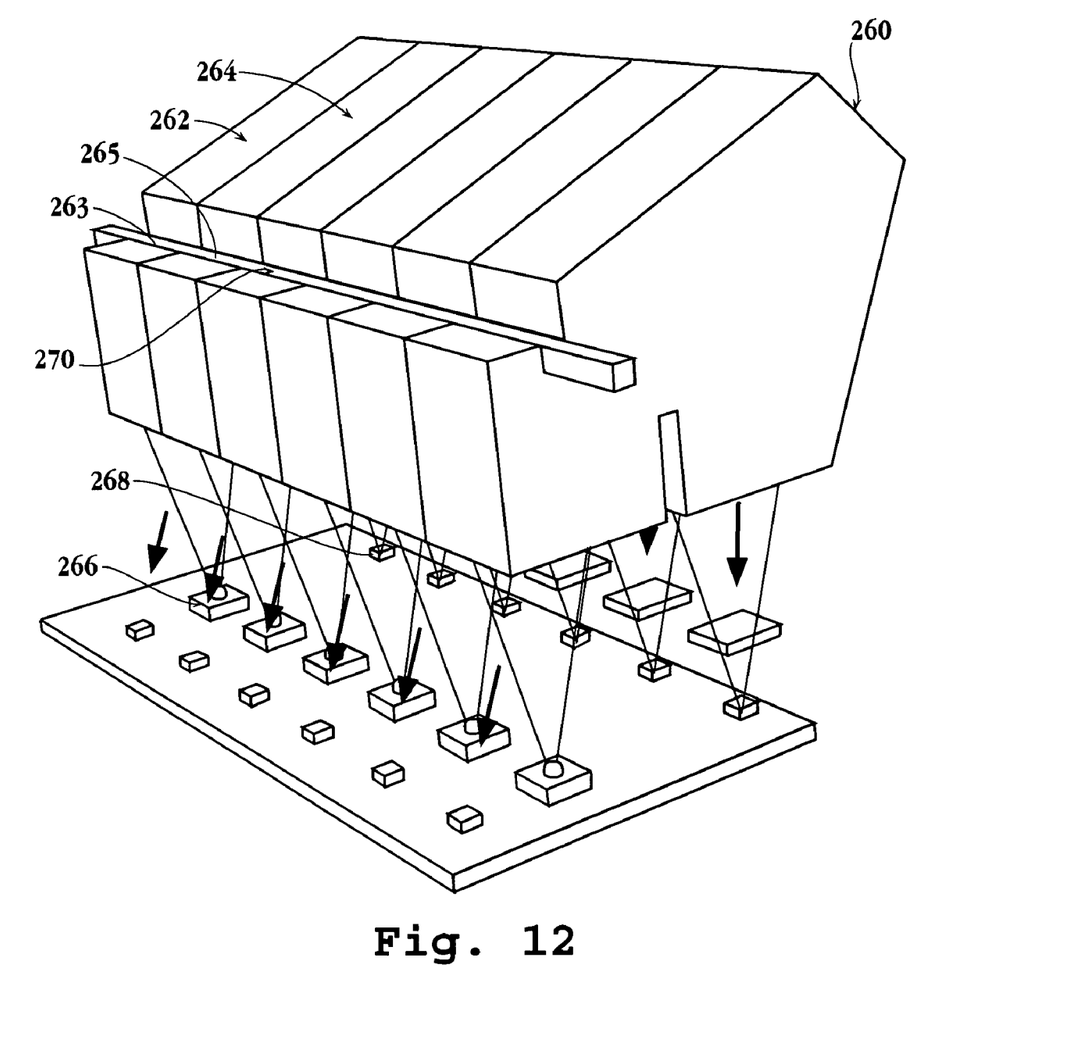
FIG. 12 is a perspective view of multiple optical modules of the type shown in FIG. 7, which are ganged together for detection of a linear array of analyte-detection zones.

Modification of the above modules to accommodate multiple samples along a direction normal to the axis of the excitation beam path is illustrated in FIGS. 11 and 12. FIG. 11 shows a optical module 230 that can accommodate four different samples at individual sample stations 234, 236, 238, 240. The cross-sectional construction of the module is the same as that of the module 206 shown in FIG. 10, and differs only in having an expanded width dimension to accommodate multiple sample stations. Each sample station, such as a 240, has its own light source, such as light source 242, each providing a pair of spaced LEDs, such as LEDs 244, 246, and its own pair of photodetectors, such as photodetectors 248, 250, and associated filters, such as filters 252, 254. The excitation and detection optics for each station are substantially as described with respect to FIG. 10.

The control unit in an assay apparatus employing module 10 operates to interrogate each sample station individually, and each LED/photodetector pair in a sample station individually, so that cross-talk between stations is never recorded, and each photodetector is seeing substantially the same solid angle of fluorescence emission. The apparatus may be used to carry out four two-wavelength fluorescence measurements on each of four samples, e.g., different dilutions of the same sample, or samples under different reaction conditions, or multiple different samples.

In an embodiment 260 shown in FIG. 12, multiple individual samples are handled by ganging multiple modules, such as modules 262, 264, together to form a linear array 270 of sample regions, such as regions 263, 265. Each of these modules, has a module 262, has its own light source, such as LED 266 and its own photodetector, such as photodetector 268, and associated bandpass filter.

It will be appreciated that the modules shown in FIGS. 11 and 12, each designed to handle a linear array of sample detection zones may be adapted for a variety of fluorescent assay formats, including a linear array of nucleic acids. Further, multiple-sample modules, such as shown in FIGS. 11 and 12, can be placed back to back to accommodate a planar array, e.g., 2×6 array, of sample zones, or modules with multiple sample regions aligned in the direction of the excitation beam axis can be ganged together to form planar sample arrays.

Although not specifically described herein, it will be apparent that the optical module of the invention may be designed using features of the upstream and downstream assemblies of the two embodiments illustrated, but in different combinations. For example, an optical assembly having the upstream subassembly construction of the "in-plane format" and the downstream assembly construction of the "out-of-plane format" would be suitable for an assay device in which the light source and detection zone are in one plane, and the photodetector in a different plane. As another example, any of the modules described above can be readily adapted to provide an elongate detection channel that would accommodate an electrophoretic column for detecting the migration of electrophoretic species at one or several interrogation zones.

What is claimed is:

1. A diagnostics apparatus for detecting fluorescence events related to the presence of an analyte in a sample applied to the apparatus, comprising
  (a) a housing,
  (b) a source of excitation light and a photodetector mounted in said housing,
  (c) a multi-surface optical module carried in said housing, adjacent said light source and photodetector, and comprising:
    (ci) an upstream portion having a first focusing surface for directing excitation light from said light source to a focal region within an analyte-detection zone in said apparatus, and
    (cii) a downstream portion having a second focusing surface and at least one reflecting surface for directing fluorescence-emission light produced by fluorescence events within said detection zone, in a direction substantially normal to the path of said excitation light within the detection zone, onto said photodetector,
  (d) a display carried on said housing, and
  (e) a microprocessor in said housing operatively coupled to:
    (ei) said excitation light source for activating the same,
    (eii) said photodetector for receiving electronic signals therefrom, and for converting said signals to an analyte-detection signal, and
    (eiii) to said display for displaying said detection signal.

2. The apparatus of claim 1, wherein said analyte-detection zone is formed in the upstream portion of said optical module, and said light source, first focusing surface and detection zone intersect a common plane.

3. The apparatus of claim 2, wherein said light source includes a pair of side-by-side sources of excitation light for directing separate, different-wavelength excitations light rays into said detection zone, and the spacing between said sources is such as to direct light from the two sources into substantially the same region of the detection zone.

4. The apparatus of claim 2, wherein said source of excitation light includes a pair of side-by-side sources of excitation light for directing separate, different-wavelength excitations light rays into said detection zone, and the focusing surface in the upstream portion is bifurcated for focusing light from the two sources into substantially the same region of the detection zone.

5. The apparatus of claim 2, wherein said analyte-detection zone is formed in said optical module, said module includes back and top faces and first and second reflecting regions within said back and top faces, respectively.

6. The apparatus of claim 5, which includes a pair of side-by-side photodetectors for detecting separate, different wavelength fluorescence emission events within said detector, the focusing surface in said downstream portion has a bifurcated surface designed to direct fluorescence emission light rays from the detection zone to each of said photodetectors, and which further includes, for each photodetector, a band-pass filter disposed between the bifurcated optical surface and the associated photodetector.

7. The apparatus of claim 5, which includes at least two side-by-side photodetectors for detecting separate, different wavelength fluorescence emission events within said detector, the top-face reflecting region is of dihedral form to direct said fluorescence emission light rays from the detection zone to each of said photodetectors, and which further includes, for each photodetector, a band-pass filter disposed between the bifurcated surface and the associated photodetector.

8. The apparatus of claim 5, which includes at least two side-by-side photodetectors for detecting separate, different wavelength fluorescence emission from said detector, the top-surface reflecting region is curved to direct said fluorescence emission within said detection zone to each of said photodetectors, and which further includes, for each photodetector, a band-pass filter disposed between the split focusing surface and the associated photodetector.

9. The apparatus of claim 2, wherein the light source and photodetector are carried on a support in said housing, and said optical module is mounted on said support.

10. The apparatus of claim 2, wherein said optical module is a disposable cartridge that is removably carried in said housing.

11. The apparatus of claim 1, wherein said detection zone is contained in a sample handling device in the apparatus, said device having fluid-handling structure for receiving a sample and directing the same to the detection zone.

12. The apparatus of claim 11, wherein said sample-handling device includes a microfluidics plate that is laminated to a surface of said optical module.

13. The apparatus of claim 12, wherein said optical module and attached sample-handling device form a disposable cartridge that is removably mounted in said housing.

14. The apparatus of claim 1, which includes a plurality of said optical modules arranged side-by-side, for detecting fluorescence events related to the presence of an analyte in a plurality of samples in a sample array.

15. The apparatus of claim 1, wherein said light source and photodetector are oriented in substantially the same direction and are disposed on opposite sides of the detection zone, and which further includes a sample-handling device having the detection zone and fluid-handling structure for receiving a sample and directing the same into the detection zone.

16. The apparatus of claim 15, wherein said a sample-handling device and optical module are sealed together in confronting relationship to form an assay cartridge that defines an enclosed fluid-handling structure having said fluid-handling structure and said analyte-detection zone.

17. The apparatus of claim 1, wherein said light source and photodetector are oriented in substantially the same direction, and are disposed on opposite sides of the detection zone, and
   (i) the upstream portion includes a first converging optical surface whose focal point is positioned at or near said light source, a second converging optical surface effective to focus excitation light from the first converging optical surface within said analyte-detection zone, and a first reflecting surface which cooperates with the second optical surface to reverse the direction of light propagating between the light source and photodetector, and
   (ii) the downstream portion includes a third converging optical surface whose focal point is positioned at or near said detection zone, and whose optical axis is substantially orthogonal to the optical axis of the second converging optical surface, a fourth converging optical surface effective to focus fluorescence light produced in the detection zone and passed through the third converging optical surface onto said photodetector, and second and third reflecting surfaces which cooperate with the third optical surface to reverse the direction of light propagating between the third optical surface and photodetector.

18. The apparatus of claim 17, wherein said light source is a light-emitting diode, and said first converging optical surface has a curvature that acts to offset light rays from the diode toward the center of the optical field formed by the optical surface, to enhance the brightness of the center region of the optical field.

19. The apparatus of claim 1, wherein said optical module is formed of a single-piece injection molded article formed of a polymer selected from the group consisting of polystyrene, polycarbonate, and polymethylmethacrylate.

20. A unitary, multi-surface optical module for use in a diagnostics apparatus intended for detecting fluorescence events related to the presence of an analyte in a sample applied to the apparatus, said module comprising, in operative condition in the apparatus,
   (i) an upstream portion having a first focusing optical surface for directing excitation light rays from a source of fluorescence-excitation light in the apparatus at a focal region within an analyte-detection zone in said apparatus, and
   (ii) formed integrally with said upstream portion, in a single-piece construction, a downstream portion having a second focusing optical surface and at least one reflecting surface for directing fluorescence-emission light rays produced by fluorescence events within said detection zone, in a direction substantially normal to said excitation light rays within the detection zone, onto a photodetector in said apparatus.

21. The module of claim 20 which is formed by injection molding a single article formed of a polymer selected from the group consisting of polystyrene, polycarbonate, and polymethylmethacrylate.

22. The module of claim 20, wherein said analyte-detection zone is formed in the upstream portion of said optical module, and said light source, first focusing optical surface and detection zone, with the optical assembly in operative condition in the apparatus, intersect a common plane.

23. The module of claim 20, wherein said analyte-detection zone is formed in said module, and said module includes back and top faces and first and second reflecting surfaces contained on said back and top faces, respectively.

24. The module of claim 23, which further includes a sample-handling device for receiving a sample and directing the same into said detection zone, said device having a microfluidics plate that is laminated to a surface of said optical assembly.

25. The module of claim 20, wherein the light source and photodetector in the apparatus are oriented in substantially the same direction, and are disposed on opposite sides of the detection zone, and
   (i) the upstream portion includes a first converging optical surface whose focal point is positioned at or near said light source, a second converging optical surface effective to focus excitation light from the first converging optical surface within said analyte-detection zone, and a first reflecting surface which cooperates with the second optical surface to reverse the direction of light propagating between the light source and photodetector, and
   (ii) the downstream portion includes a third converging optical surface whose focal point is positioned at or near said detection zone, and whose optical axis is substantially orthogonal to the optical axis of the second optical surface, a fourth converging optical surface effective to focus fluorescence light rays produced in the detection zone and passed through the third converging optical surface onto said photodetector, and second and third reflecting surfaces which cooperate with the third optical surface to reverse the direction of light between the third optical surface and photodetector.

* * * * *